United States Patent
Hatangadi et al.

(10) Patent No.: US 6,726,631 B2
(45) Date of Patent: Apr. 27, 2004

(54) FREQUENCY AND AMPLITUDE APODIZATION OF TRANSDUCERS

(75) Inventors: Ram Hatangadi, Chandler, AZ (US); Patrick Pesque, Scottsdale, AZ (US); Sanjay Chandran, Tempe, AZ (US)

(73) Assignee: GE Parallel Designs, Inc., Tempe, AZ (US)

(*) Notice: Subject to any disclaimer, the term of this patent is extended or adjusted under 35 U.S.C. 154(b) by 111 days.

(21) Appl. No.: 09/954,563

(22) Filed: Sep. 17, 2001

(65) Prior Publication Data

US 2002/0042577 A1 Apr. 11, 2002

(51) Int. Cl.[7] ................................. A61B 8/00
(52) U.S. Cl. ................... 600/459; 29/25.35; 310/334
(58) Field of Search .................... 367/140, 152, 367/153, 155; 310/320, 357, 334–336; 686/437; 600/459, 443; 128/662.03; 29/25.35

(56) References Cited

U.S. PATENT DOCUMENTS

| | | | |
|---|---|---|---|
| 4,518,889 A | * 5/1985 | 'T Hoen | 310/357 |
| 4,586,512 A | * 5/1986 | Do-huu et al. | 600/447 |
| 4,841,492 A | 6/1989 | Russell | |
| 5,285,789 A | 2/1994 | Chen et al. | |
| 5,329,496 A | * 7/1994 | Smith | 367/140 |
| 5,479,926 A | 1/1996 | Ustuner et al. | |
| 5,511,550 A | 4/1996 | Finsterwald | |
| 5,553,035 A | * 9/1996 | Seyed-Bolorforosh et al. | 367/140 |
| 5,902,242 A | 5/1999 | Ustuner et al. | |
| 5,916,169 A | * 6/1999 | Hanafy et al. | 600/459 |
| 5,938,612 A | * 8/1999 | Kline-Schoder et al. | 600/459 |
| 6,057,632 A | * 5/2000 | Ustuner | 310/334 |

OTHER PUBLICATIONS

J. Sato, et al., "Dependence of the electromechanical coupling coefficient on the width-to-thickness ratio of plank-shaped piezoelectric transducers used for electronically scanned ultrasound diagnostic systems", J. Acoust. Soc. Am. 66(6), Dec. 1979, pp. 1609–1611.

M. O'Donnell, et al., "Kramers–Kronig relationship between ultrasonic attenuation and phase velocity", J. Acoust. Soc. Am. 69(3), Mar. 1981, pp. 696–701.

* cited by examiner

Primary Examiner—Francis J. Jaworski
(74) Attorney, Agent, or Firm—Peter J. Vogel; Armstrong Teasdale LLP

(57) ABSTRACT

A method and apparatus for apodization is exemplified in an ultrasound transducer used, for example, in medical applications. The method and apparatus of the present invention provides an ultrasonic transducer with frequency and amplitude apodization, thus improving signal quality and producing improved ultrasonic images. The manufacture of this apparatus is improved by the making of composite cuts into piezoelectric material according to a predetermined pattern which generally varies the concentration of piezoelectric material across the surface of the transducer. Concentration of piezoelectric material can be varied across the surface of the piezoelectric transducer by varying the spacing between the cuts in the piezoelectric material, or by varying the width of the cuts in the piezoelectric material, or a combination of both.

19 Claims, 13 Drawing Sheets

Beam Width vs Depth, Frequency Apodized vs non-Frequency Apodised

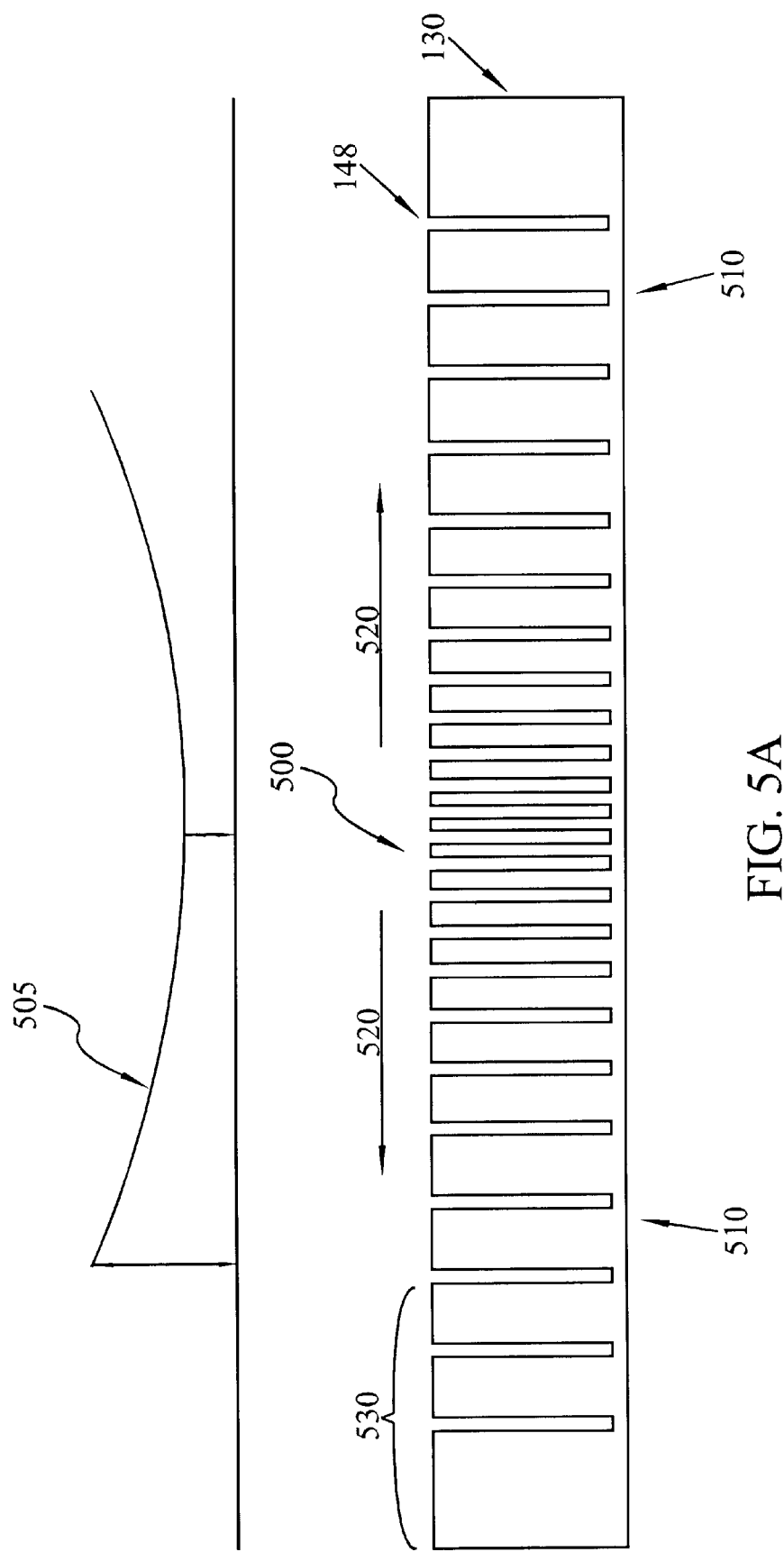

FREQUENCY AND AMPLITUDE APODIZATION OF TRANSDUCERS

BACKGROUND OF THE INVENTION

This invention relates generally to transducers and transducer arrays and, more particularly, to ultrasonic transducer arrays such as those used in medical imaging. Various aspects of the invention also relate to a method of manufacturing apodized transducers.

A transducer converts energy from one form into another form (for example, from mechanical energy to electrical energy or vice versa). Transducers in audio loudspeakers, for example, convert electrical signals into mechanical vibrations that in turn create audible sound waves. Similarly, transducers are often used to generate high frequency ultrasonic waves for various applications such as medical imaging, non-destructive evaluation (NDE), fluid flow sensing, non-invasive surgery, dentistry and the like. Transducers are widely used in the field of medicine for investigative purposes. For example, an ultrasound transducer makes it possible to observe the development of a baby in its mother's womb. This non-intrusive procedure assists doctors in estimating the date that the child will be born, and in verifying the proper development of the baby by noting, for example, details as tiny as the four chambers of the heart and the development of the lungs. This medical advance is facilitated by ultrasonic sound waves which are transmitted by the transducer and which are variably reflected off of varying types of tissue inside the body. The transducer receives these reflected ultrasonic signals and converts these ultrasonic signals into electrical signals which can be used to generate, for example, a two-dimensional picture of a baby or organs within the human body.

Ultrasonic technology has made large technological advances in recent years. For example, one kind of transducer that has experienced technological advances is a Brightness mode transducer (B-Mode). In a B-mode transducer, the amplitude of reflected pulses (i.e. the strength of a reflected ultrasonic signal) is indicated by the brightness of a dot. By scanning an entire area of interest, multiple dots are combined to map out an image for display. The area of interest can be scanned, for example, by moving the transducer linearly or in an arc like motion. Until the 1970's, virtually all B-mode imaging systems required several seconds to produce an image. Consequently, these systems were limited to imaging non-moving targets. Since that time, rapid two-dimensional B-mode imaging, known as "real-time scanning", has enabled visualization of moving targets within the body. In order to create a useful display of the moving targets within the body, methods were developed to rapidly move the acoustic beam throughout the area of interest inside the body. Three primary methods have been developed to rapidly move the acoustic beam: mechanical sector scanners, sequential linear arrays, and phased linear arrays. Mechanical sector scanners rapidly move the acoustic beam using one or more piston transducers which may be rocked or rotated about a fixed axis with, for example, an electric motor. Linear arrays generally consist-of a number of small individual transducers arranged side-by-side in a single assembly. Sequential linear arrays typically produce two-dimensional images in a rectangular format by transmitting on each of the array elements (or small groups of elements) and receiving the echo information with the same elements. Phased array scanners are the most sophisticated real-time systems. Phased array systems produce images by rapidly steering the acoustic beam through the target by electronic rather than mechanical means. The phased array scanners produce the pie-shaped image commonly seen in medical ultrasound applications, and popularly known as the "sector-scan". These three systems have been generally described by Somer and Von Ramm.

Obviously, the ability to have a high quality resolution is important to producing accurate and readable images. There are three aspects of resolution which are relevant to ultrasound imaging: spatial resolution, contrast resolution, and temporal resolution. Spacial resolution generally refers to the ability to distinguish registrations in the displayed image of objects that are close together. Contrast resolution generally refers to the ability to produce distinguishable differences in the brightness of two different types of materials which would have slightly different echogenicities. For example, a tendon might reflect at a different brightness than a muscle. Temporal resolution refers to the ability to display an image when the object being imaged is moving.

One of the factors that interferes with achieving high resolution in these areas is the fact that the ultrasound signal undergoes attenuation and dispersion as it progresses deeper into tissue. This degradation is governed by the Kramer-Kronig relationships. See, M. O'Donnel, E. T. Jaynes, and J. G. Miller, *Kramer-Kronig, Relationship Between Ultrasonic Attenuation And Phase Velocity*, J. Acoust. Soc. Am. 69(3), March, 1981, pp. 696–701. One method of improving resolution is to frequency apodize the transducer aperture. A previous attempt to achieve this frequency apodization is described by U.S. Pat. No. 5,902,242. In this patent, the central zone of the array element is thin (elevation direction) and gradually thickens nearer the edges of the aperture. Two ultrasonic images are created using a first relatively high ultrasonic imaging bandwidth transmit pulse and a second narrower bandwidth transmit pulse. The first pulse activates the full aperture and creates an image that has relatively high axial resolution and relatively low elevational resolution. The second pulse activates the narrower width portion of the aperture and creates an image that has relatively lower axial resolution and a higher elevational resolution at ranges spaced from the geometric focus. Combining these two frames yields an image which has both enhanced spatial and contrast resolution. This method, however, offers some significant manufacturing challenges. The general functionality disclosed in U.S. Pat. Nos. 5,902,242 and 5,479,926 are incorporated herein by reference.

Another factor that interferes with achieving higher resolution is the existence of "side lobes" in the ultrasonic beam. When an ultrasonic beam passes through a human body or other medium, "blurring" occurs as the beam is defracted (i.e. bent) creating side portions (i.e. "side lobes") which accompany the desired main lobe of the ultrasonic beam. The side lobes act as interference and tend to degrade the ability to achieve high resolution. Past attempts have been made to suppress the side lobes. One conventional method of suppressing side lobes is to apply an amplitude apodization function to the electrical signal, usually a Gaussian or Hanning function, to shape the electrical signals received by the array. (See, for example, Apodization of Ultrasound Transmission, U.S. Pat. No. 4,841,492 incorporated herein by reference.) An apodization function is applied to smoothly taper down to zero the edges of a sampled region of a signal. This electrical signal apodization has several undesirable aspects. For example, while in-plane (azimuth direction) electrical signal apodization is possible, out-of-plane (elevation direction) electrical signal apodization may not be possible in a 1D arrays because one signal connects across the whole elevation aperture. Although out-of-plane electrical signal apodization could possibly be done for 2D arrays, where the elevation aperture is discretized and can be electrically addressed individually, this may be quite difficult to achieve due to the electrical complexity, muxing, etc.

Another method of achieving amplitude apodization is to place a thin sheet of acoustic blocking layer over the front surface of the transducer to substantially block the ultrasonic wave emission from a portion of the front surface area, thus defining an inactive area. (See, generally, Ultrasonic Transducer Apodization Using Acoustic Blocking Layer, U.S. Pat. No. 5,285,789, incorporated herein by reference.) This approach generally removes the edges of the transducer from operation and has the effect of suppressing the side lobes. There are at least two problems with this approach: the first is that an extra layer is typically added to the transducer stack making manufacture more difficult, and the second is a loss of sensitivity due to blocking of the aperture (reducing the strength of the signal which can be converted to an electrical signal).

Another method of achieving side lobe suppression is to apply different levels of polarization across the transducer elevation. In this way, segments of the transducer near the center are polarized much more strongly than other transducer elements near the edges of the transducer. This has the effect of suppressing the side lobes at the outer edges and transmitting somewhat amplified main lobe signals. The disadvantage of this method is that it is typically difficult to manufacture. Polarization generally requires a difficult process of applying a voltage across each individual transducer element. Because this process is typically very sensitive, breakage is more likely to occur, resulting in ruining the transducer.

Another method of suppressing side lobes involves the construction of a transducer from individual piezoelectric ceramic rods which are positioned so as to create a mechanical apodization. This is typically done by placing more ceramic rods near the center of the transducer than near the edges of the transducer. More of the sound waves, therefore, are transmitted near the center and thus the main lobe is transmitted and the side lobes are suppressed. (See Piezoelectric Apodized Ultrasound Transducers, U.S. Pat. No. 4,518,889 incorporated herein by reference.) The major disadvantage of this method is that manufacturing of such a transducer is typically extremely difficult. It can be difficult to individually place the ceramic rods in an inert binder and, furthermore, it is generally difficult to make electrical connections to the back of each individual ceramic rod. This drastically increases the chances of breaking one or more rods and destroying the transducer.

Another method of suppressing side lobes involves select removal of the metalization electrode from the outer edges of each element of the piezoelectric material. In effect, the piezoelectric rods exist in an even pattern but some of them are not connected or are only weakly connected. This creates an apodization attenuation function which modifies the ultrasound beam in the elevation plane. (See Ultrasonic Transducer Array With Apodized Elevation Focus, U.S. Pat. No. 5,511,550, incorporated herein by reference.) The disadvantage of this method is that selective removal of the metalization electrode from the transducer leaves discreet boundaries between the metalization and non-metalization areas which causes undesirable edge effects in the electric field density.

Therefore, despite all the attempts to create an improved ultrasound resolution through frequency and amplitude apodization, there still remains a need for a way to manufacture an ultrasound transducer with frequency and/or amplitude apodization capabilities which nonetheless does not involve the difficulties of manufacturing mentioned above.

SUMMARY OF EXEMPLARY EMBODIMENTS

A new method and apparatus for apodization is exemplified in an ultrasound transducer used, for example, in medical applications. Various embodiments of the method and apparatus enable the ultrasound transducer apparatus to modulate the resonance frequency across the aperture or suppress side lobes; thus improving signal quality and making it possible to produce improved images. The manufacture of this apparatus may be improved by the making of composite cuts in the piezoelectric material according to a specific pattern which generally provides a lesser/greater concentration of piezoelectric material near the middle of the transducer and more/less material near the edges of the transducer or vise versa. Concentration of piezoelectric material can be varied across the surface of the piezoelectric transducer by varying the spacing between the cuts in the piezoelectric material, or by varying the width of the cuts in the piezoelectric material, or a combination of both. Increasing the concentration of piezoelectric material near the edges as compared to the center effectively frequency modulates the ultrasound signal across the aperture. In this embodiment, some amplitude apodization may also be achieved. Alternatively, reducing the concentration of piezoelectric material near the edges of the transducer in comparison to the center effectively lessens the impact of side lobe signals. Therefore, by varying the size of composite cuts, and/or the spacing between the cuts, frequency and/or amplitude apodization may be achieved, improving signal quality, while maintaining a simple method of manufacturing.

BRIEF DESCRIPTION OF THE DRAWINGS

FIG. 5A is a side section view of an exemplary embodiment of an ultrasonic transducer.

DETAILED DESCRIPTION OF EXEMPLARY EMBODIMENTS

Various aspects of the present invention may be described herein in terms of functional block components and various processing steps. It should be appreciated that such functional blocks may be realized by any number of hardware and/or software components or computer systems configured to perform the specified functions. For example, the present invention may employ various computer systems, e.g., personal computers, workstations, and the like, which may carry out a variety of functions under the control of one or more microprocessors or other control devices. Similarly, the software elements of the present invention may be implemented with any programming or scripting languages such as C, C++, Java, Assembly Language, PERL, or the like, or any combination thereof, with the various algorithms being implemented with any combination of data structures, objects, processes, routines or other programming elements. Further, it should be noted that the present invention may employ any number of techniques for data transmission, signaling, data processing, and the like.

It should be appreciated that the particular implementations shown and described herein are illustrative of exemplary embodiments of the invention, and are not intended to limit the scope of the invention in any way. Indeed, for the sake of brevity, conventional ultrasonic devices and other functional aspects of the systems (and components of the individual operating components of the systems) may not be described in detail. Furthermore, the connecting lines shown in the various figures contained herein are intended to represent exemplary functional relationships and/or physical or logical couplings between the various elements. It should be noted that many alternative or additional functional relationships, physical connections or logical connections may be present in a practical ultrasonic system.

Figure 1:
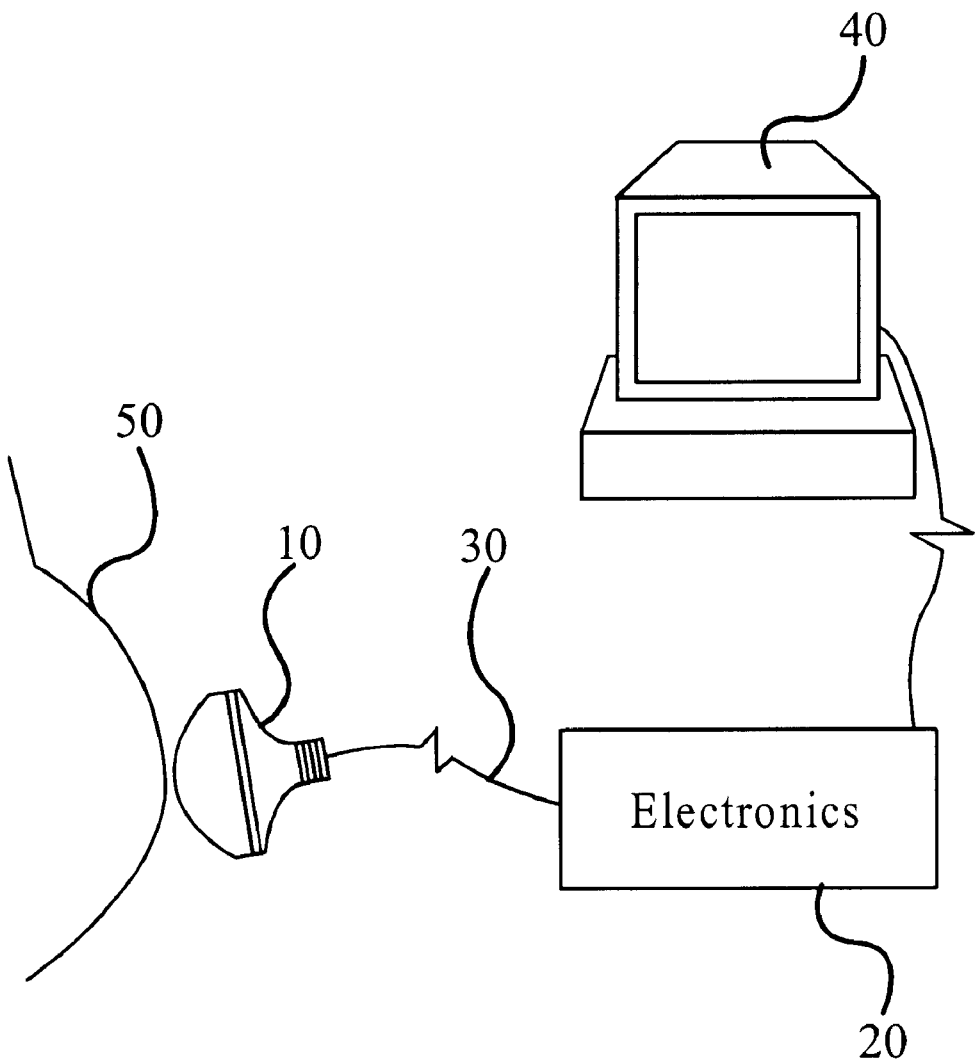
FIG. 1 is an isometric view of an exemplary ultrasound device.

A block diagram of an exemplary conventional ultrasonic transducer 10 is shown in FIG. 1. Transducers generally create ultrasonic vibrations through the use of piezoelectric materials, such as certain forms of crystals (e.g., quartz) or ceramic polymers. Piezoelectric materials vibrate in response to alternating voltages of certain frequencies applied across the material. For example, Ultrasonic Transducer Array and Manufacturing Method Thereof, U.S. Pat. No. 5,637,800, incorporated herein by reference, discloses a transducer suitable for medical use that includes arrays of piezoelectric elements. In one exemplary embodiment, transducer 10 is suitably placed in contact with the abdomen of a pregnant woman for imaging the fetus inside her body. Such a transducer is typically connected to electronics 20 that drive the transducer via a coaxial cable 30 or the like. The electronics 20 are typically connected to a display 40 to visually display images created based upon signals received from ultrasound transducer 10.

Although the invention disclosed herein is primarily discussed in terms of a piezoelectric assembly for a medical imaging transducer, any number of other embodiments fall within the ambit of the present invention. For example, the devices and techniques described herein could be used in conjunction with other types of transducer systems, such as audio loud speakers, nondestructive evaluation (NDE), non-invasive surgery, dentistry, SONAR, radio wave transmission and reception, magnetic transmission and reception Magnetic Resonance Imaging (MRI), harmonic imaging, microwave transmission and reception and optical defraction gratings. For example, in harmonic imaging, transmission occurs at lower frequencies than the reception of returning signals and typically apodization is required to obtain usable images in this process. Moreover, the spatial relationships described herein and the drawing figures are merely for illustrative purposes and, many spatial arrangements could be formulated within the ambit of the present invention. Furthermore, the materials described, such as the piezoelectric material are exemplary in nature and the materials described herein could be replaced by any number of equivalent materials typically used in transducer-related fields, such as the above mentioned fields.

Figure 2:
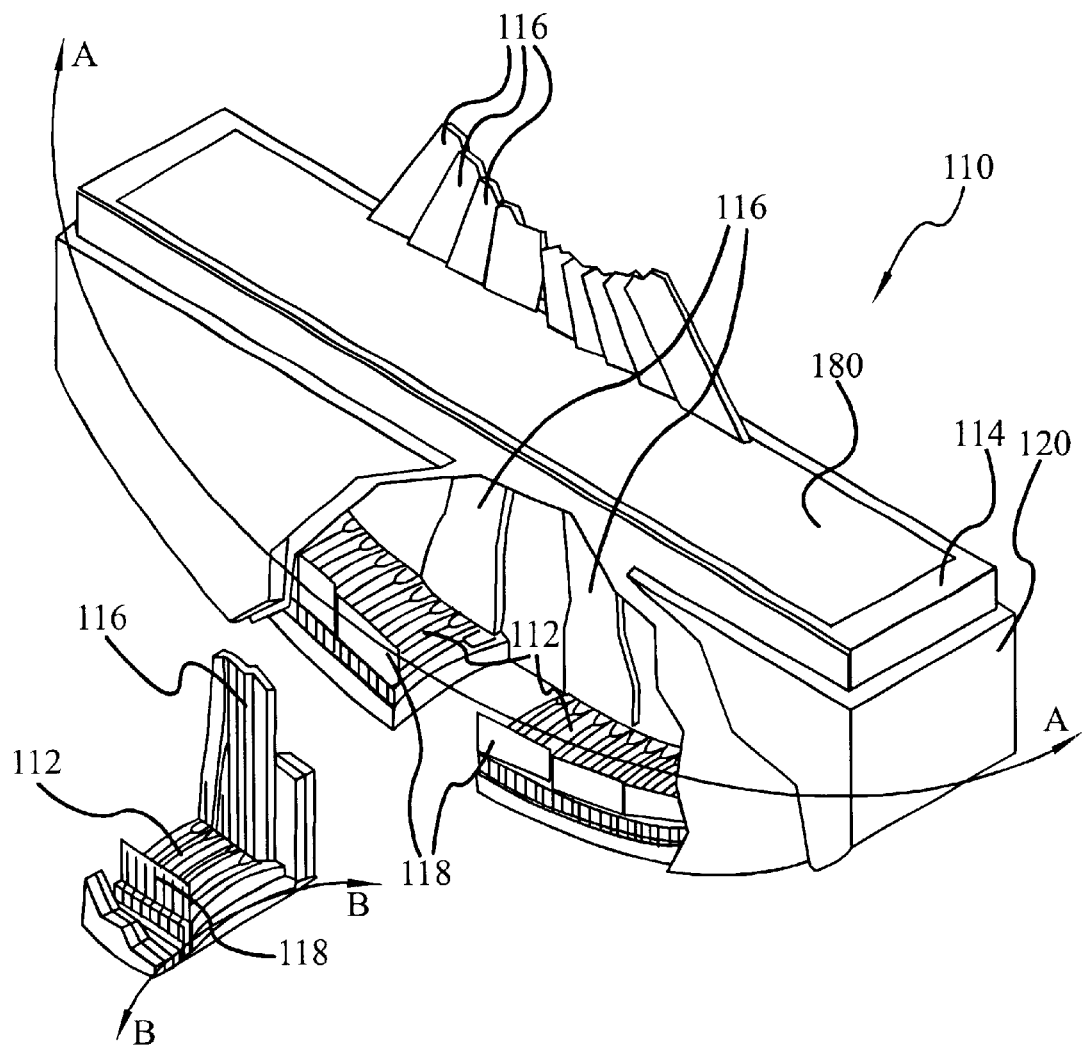
FIG. 2 is an isometric view of an exemplary ultrasound device.

With reference to FIG. 2, an ultrasonic transducer array 110 suitably includes one or more individual ultrasonic transducer elements 112 encased within a housing 114. The individual elements may be electronically connected to the leads 116 of a flexible printed circuit board and ground foils 118 that are fixed in position by a polymer backing material 180. A dialectic base layer 120 is formed around the array of transducer elements and the housing.

Figure 2A:
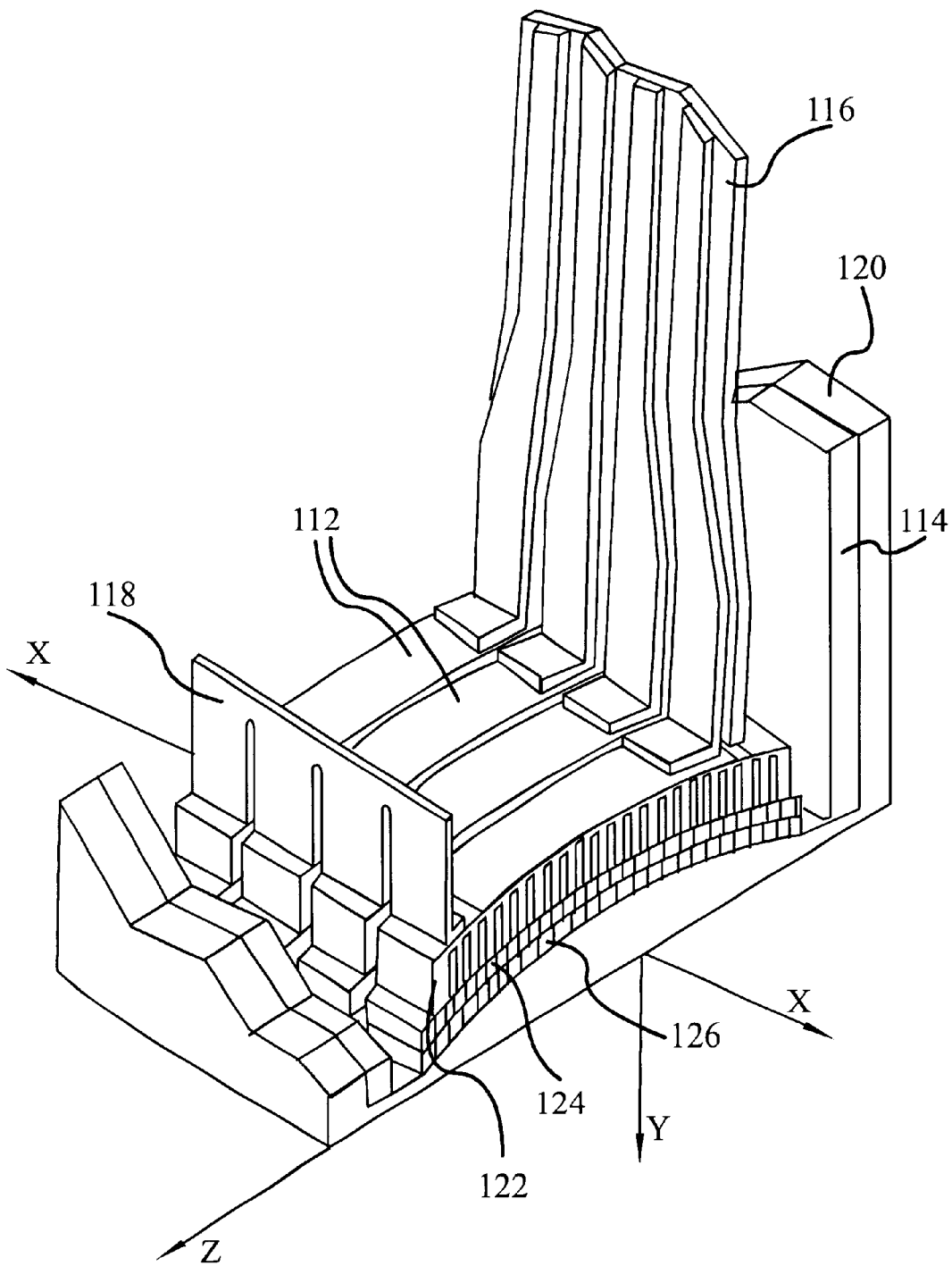
FIG. 2A is an isometric view of a portion of an exemplary ultrasound device.

With reference to FIG. 2A, each individual ultrasonic transducer element 112 includes a piezoelectric layer 122, a first acoustic matching layer 124 and a second acoustic matching layer 126. An array axis is provided in the X direction as shown. A Y axis is perpendicular to the X axis and perpendicular to the plane defining a front surface of the transducer housing as shown. The individual elements may be mechanically focused into a desired imaging plane (defined by the x-y axes) by the concave shape of the piezoelectric and adjoining acoustic matching layers. The individual matching elements may also be mechanically isolated from each other along an array axes A located in the imaging plane (as may be defined by the midpoints of the cords extending between the ends of each transducer element). Front surfaces of the piezoelectric layer 122 and acoustic matching layers 124, 126 may be concave in the direction of an axes B perpendicular to the array axes A to aid in the focusing of acoustic energy. In one embodiment, the array axes A has a convex shape to enable sector scanning. However, the array axes may be linear or curved or may have a combination of linear parts and curved parts.

Figure 3:
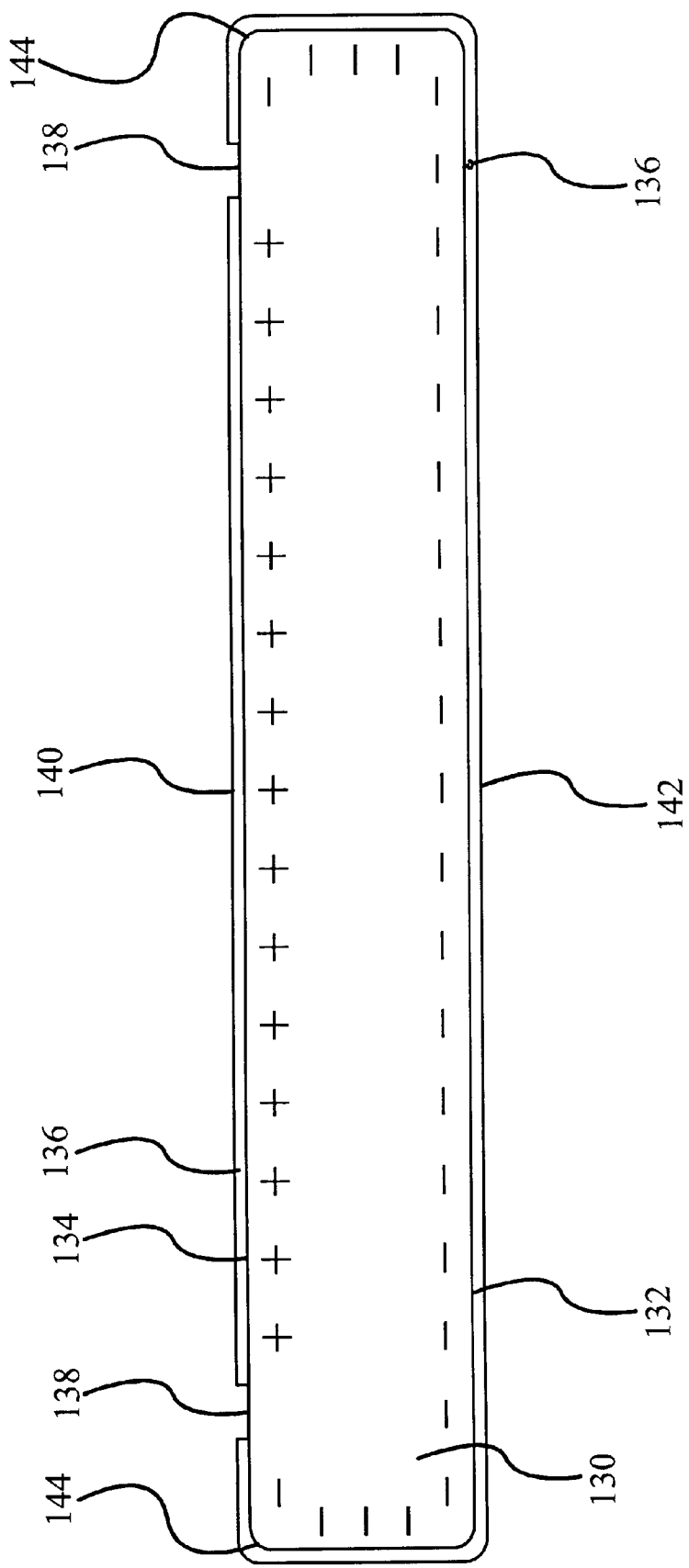
FIG. 3 is a cross sectional end view of an exemplary piezoelectric substrate.

An array of individual ultrasonic transducer elements may be made according to any technique. With reference to FIG. 3 for an exemplary technique for making transducer elements, a piece of piezoelectric ceramic material is ground flat and cut to a rectangular shape to form a substrate 130 having a front surface 132 and a rear surface 134. Substrate 130 may be shaped to be generally rectangular, although substrates of other geometric configurations can be used in alternate embodiments. An exemplary substrate 130 has dimensions of approximately 13 mm×38 mm×0.175 mm, although substrates of any size can be used in alternate embodiments.

One example of a suitable piezoelectric ceramic material is type 3203HD material made by Motorola Ceramic Products of Albuquerque, N.Mex., which exhibits high density and strength characteristics that allow the cutting step (described below) to be made without fracturing the individual elements. It will be further appreciated that a variety of piezoelectric materials may be used, including ceramics (e.g., lead zinconate, barium titanate, lead metaniobate, and lead titanate), piezoelectric plastics (e.g., PVDF based polymer and PVDF-TrFe co-polymer), composite materials (e.g., 1–3 PZT/polymer composite, PZT powders dispersed in polymer matrix base (0–3 base composite), base and compounds of PZT and PVDF or PVDF-TrFe), or relaxor ferroelectrics (e.g., PMN: PT).

Piezoelectric substrate 130 may be further prepared by applying a metalization layer 136, such as by first etching the surfaces with a 5% fluoboric acid or plural boric acid solution and then electroless nickel plating using commonly available commercial plating materials and techniques. Other methods may be substituted for plating or coating the piezoelectric substrate such as vacuum deposition of these and other metals, spray coating, or other similar methods.

This conductive coating suitably covers at least a portion of the substrate 130 to provide electrical excitation to the piezoelectric material. The metalization layer 136 may be formed from any sort of metal or other electrical conductor. Suitable coatings may include chromium, gold, silver, nickel, copper, aluminum, tin, various forms of solder, and the like. Alternatively, various conducting or nonconducting materials may be combined or formed in combination on the surface of substrate 130 to create metalization layer 136. As shown in FIG. 3, the plating material may extend completely around all the surfaces of the piezoelectric substrate. In one embodiment, not shown, a subsequent copper layer (approximately 2 micron thickness) is electroplated onto a first nickel layer (approximately 1 micron thickness) followed by a thin layer of electroplated gold (>0.1 micron thickness) to protect against corrosion.

Metalization layer 136 is isolated to form two electrodes by making at least two gaps or isolation cuts 138 through the metalization layer 136 on the rear surface 134 of the piezoelectric substrate. A wafer dicing saw may be used for this purpose. Other methods could also be used to isolate the metalization layer, for example, gaps 138 can be created by placing a tape or mask of any suitable material on substrate 130 in the locations where gaps 138 are desired, such that the conductive material is easily removed after plating, or such that conductive material does not adhere to substrate 130 in certain locations in other embodiments.

The two isolation cuts 138 form a rear surface electrode 140 and a front surface electrode 142. The front surface electrode includes wrap around ends 144 that extend from the front surface 132 around to the rear surface 134 of the piezoelectric substrate. The wrap-around ends 144 in one embodiment may extend approximately 1 mm along each side of the rear surface.

Rear electrodes 140 and front electrode 142 are thereby separated electrically by piezoelectric substrate 130, which has a capacitance, for example, of approximately 400 pF at 1 kHz. When an electric potential is applied across electrodes 140 and 142 at the proper frequency for the particular substrate material, piezoelectric substrate material 130 vibrates, thus generating sound waves of a corresponding frequency. For example, an exemplary embodiment using 3203HD ceramic generates ultrasound waves at a center frequency of 3.5 MHz.

Figure 4:
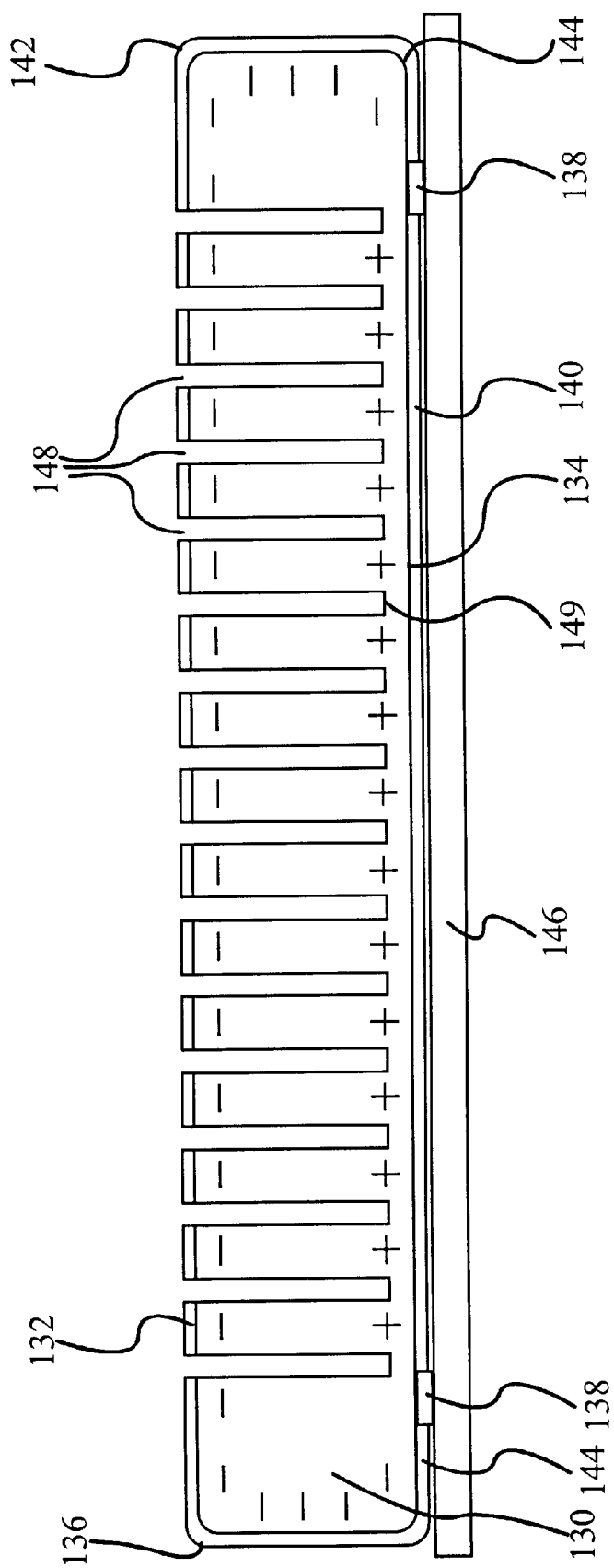
FIG. 4 is a cross sectional end view of an exemplary piezoelectric substrate having a series of composite cuts.

In alternate embodiments, (not shown), the transducer may be composed of multiple piezoelectric assemblies suitably joined with an adhesive or other joining method to form a stack of piezoelectric assemblies. In this embodiment, the individual layers of the piezoelectric assemblies have electrical nodes arranged such that common negative and positive electrical nodes are established throughout the stack of piezoelectric assemblies. FIGS. 3 and 4 show exemplary positive and negative nodes.

With reference to FIG. 4, metallized and isolated piezoelectric substrate 130 is prepared for cutting by turning it over and mounting rear surface electrode 140 to a carrier film 146, such as an insulating polyester film. A thermoplastic adhesive or other suitable attachment may be used to affix the piezoelectric substrate 130 to carrier film 146. Using a wafer dicing saw or other cutting tool, or other cutting tool, a series of composite cuts 148 may be made most of the way through the piezoelectric substrate 130 leaving only a small amount, for example, 50 microns, of substrate material uncut between an inner end 149 of the composite cut and the rear surface 134 of the substrate. These saw cuts are known as composite cuts 148 because the cuts are generally subsequently filled with a material such as epoxy, thus creating a composite ceramic/epoxy structure.

Alternatively, the composite cuts may be made through the substrate 130, including into, but not all the way through, the rear surface electrode 140. Providing multiple composite cuts through substrate 130 allows piezoelectric substrate 130 to be curved or concavely formed as desired. Alternatively, the piezoelectric substrate may be left flat. The arrangement and layout of composite cuts 148 is further described below. Composite cuts 148, may also perform the function of reducing lateral resonance modes in the completed device. In this regard the cuts may be filled with a low durometer, lossy material such as epoxy. The epoxy may be chosen to minimize clamping between the posts and, thus, allow the maximum freedom and independence for each piezoelectric finger of material. For example, an epoxy may have properties that attenuate sound energy and reduce inter-post cross talk.

Figure 2B:
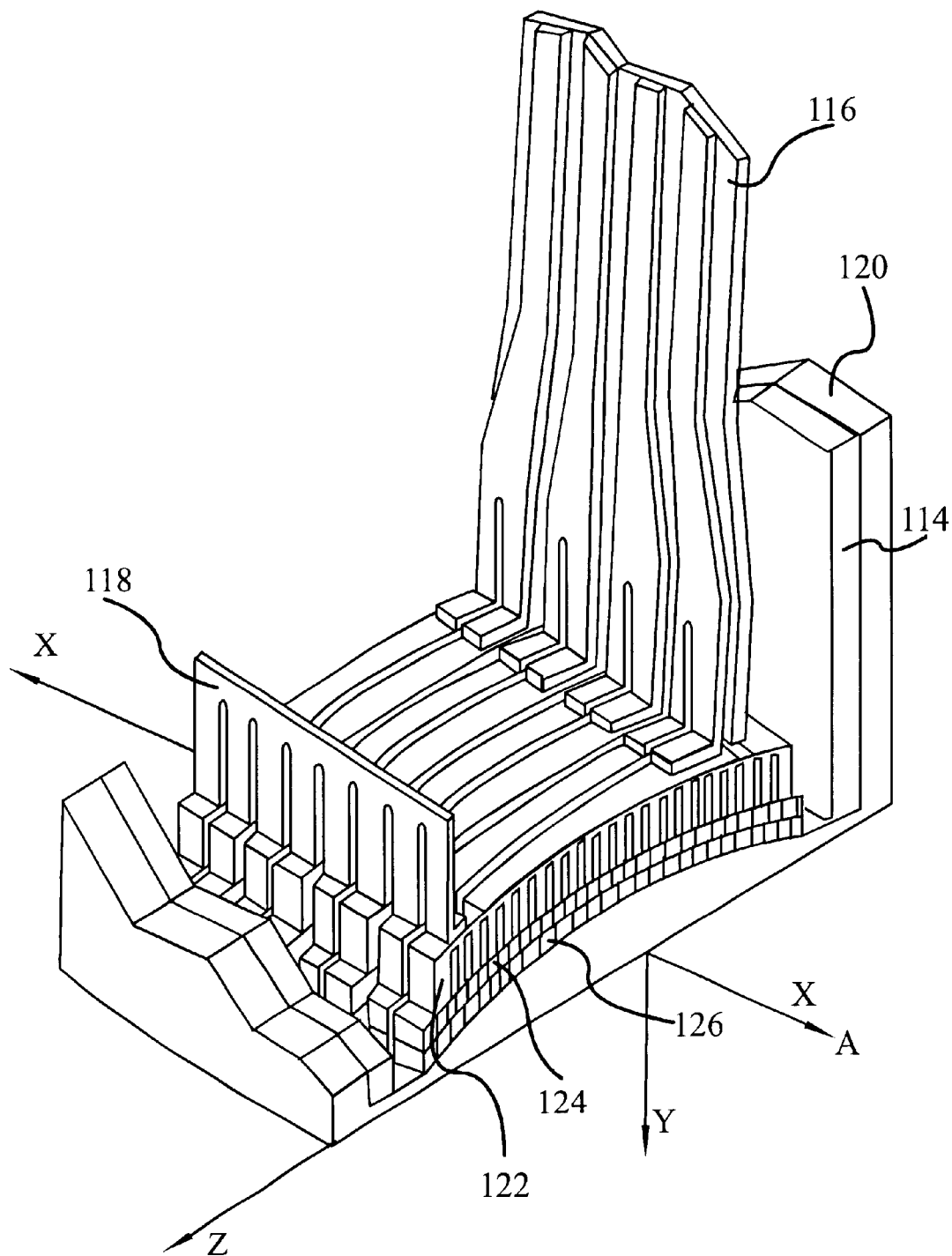
FIG. 2B is an isometric view of a portion of an exemplary ultrasound device.

It should further be appreciated that composite cuts may be made in not only the direction of the array axis X, but may also be made in the Z direction as shown in FIG. 2B, thus creating an ultrasonic transducer array having individual transducer elements that are acoustically isolated from each other along the array axis and are also separated from each other by cutting substantially through the piezoelectric substrate and matching layers to form independent piezoelectric elements. In some embodiments, the use of an acoustic lens can be avoided by using ultrasonic transducer arrays with individual transducer elements that are mechanically focused along with adjacent, similarly concave, uniform thickness, acoustic matching layers.

Ultrasound image resolution, as mentioned above, can be improved through frequency and amplitude apodization. For example, one method of frequency apodizing the transducer aperture is to cause the central aperture to resonate at a higher frequency than the edges of the aperture. This may improve the resolution in the near-field (fresnel zone) and also the far-field (franhoffer zones). The resonant frequency of vibration is inversely proportional to the width/height ratio of piezoelectric ceramic posts. See, J. Sato, M. Kawabuchi, A. Fukumoto; *Dependence Of The Electromechanical Coupling Coefficient On The Width To Thickness Ratio Of Plank Shaped Piezoelectric Transducers Used For Electronically Scanned Ultrasound Diagnostic Systems*; Journal of Acoustics Society of America (JASA) 66(6); December, 1979. According to this reference, the wave number (which is related to central resonance frequency) reduces as the width/height ratio of the composite posts increases.

In an exemplary embodiment, a composite piezoelectric substrate may be made with narrower posts at the center and wider posts at the edges. In this embodiment, the width-to-height ratio for each composite post increases from the center to the edges. In other words, the width is small at the center so the width-to-height ratio is small and as the width is increased towards the edges, the width-to-height ratio is also increased. Therefore, in this embodiment, the posts in the middle of the elevation aperture resonate at a higher frequency than those at the edges of the aperture. This provides a frequency apodization effect which can be utilized by appropriate system excitation protocols to obtain higher spacial and contrast resolution ultrasound images.

This "narrow post middle to wider post edge" embodiment may also provide an amplitude apodization effect. The amplitude apodization effect is due to the change in acoustic impedance across the elevation aperture. Because the composite cut pitch is smaller in the middle than at the edges, the acoustic impedance is lower in the middle than at the edges of the aperture. A lower acoustic impedance in the center provides more efficient impedance matching and a reduced reflection coefficient in the center than at the edges of the aperture. This provides an amplitude apodization effect and may be utilized by appropriate system excitation protocols to obtain higher resolution ultrasound images.

This amplitude apodization effect, however, may be somewhat dampened, in this exemplary embodiment, due to the slight increase in the electromechanical coupling coefficient from the center to the edges of the aperture. This reduction occurs because the electro-mechanical coupling coefficient (kt) increases as the width to height ratio increases. See, Sato. It will be noted that this electromechanical coupling coefficient relationship to the width to height coefficient is true over certain ranges of width to height coefficients as specified in the Sato reference. In another exemplary embodiment, amplitude apodization may be achieved when the pattern of composite cut pitches is reversed, i.e. wider composite posts in the middle and narrower posts nearing the edges. Amplitude apodization may be achieved in this embodiment because the ceramic fill ratio is larger in the middle as compared to the edges and amplitude sensitivity tracks ceramic fill ratio.

Figure 5B:
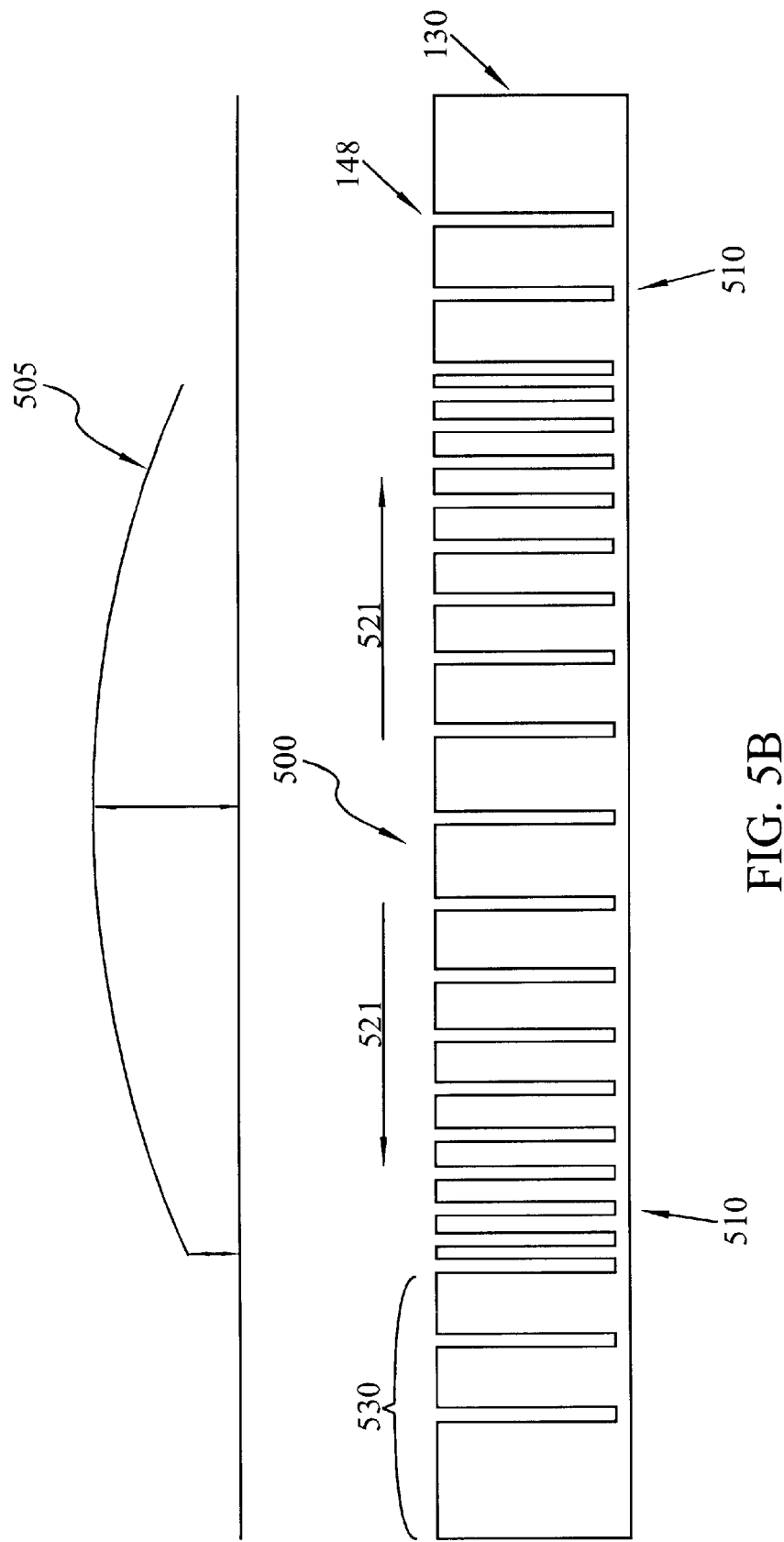
FIG. 5B is a side section view of an exemplary embodiment of an ultrasonic transducer.

A method of forming cuts in piezoelectric substrate 130 is now described in further detail. As mentioned above, it is desirable to design a transducer that is simple to manufacture and durable, and that will mechanically perform frequency and/or amplitude modulation. With reference to FIGS. 5A and 5B, composite cuts 148 are made into piezoelectric substrate 130. Curve 505, in FIGS. 5A and 5B, symbolically represents the variation in pitch across the piezoelectric substrate 130. Curve 505 may be, for example, a Gausian or Hanning type distribution and may also represent the concentration of composite material in the piezoelectric substrate.

Figure 6:
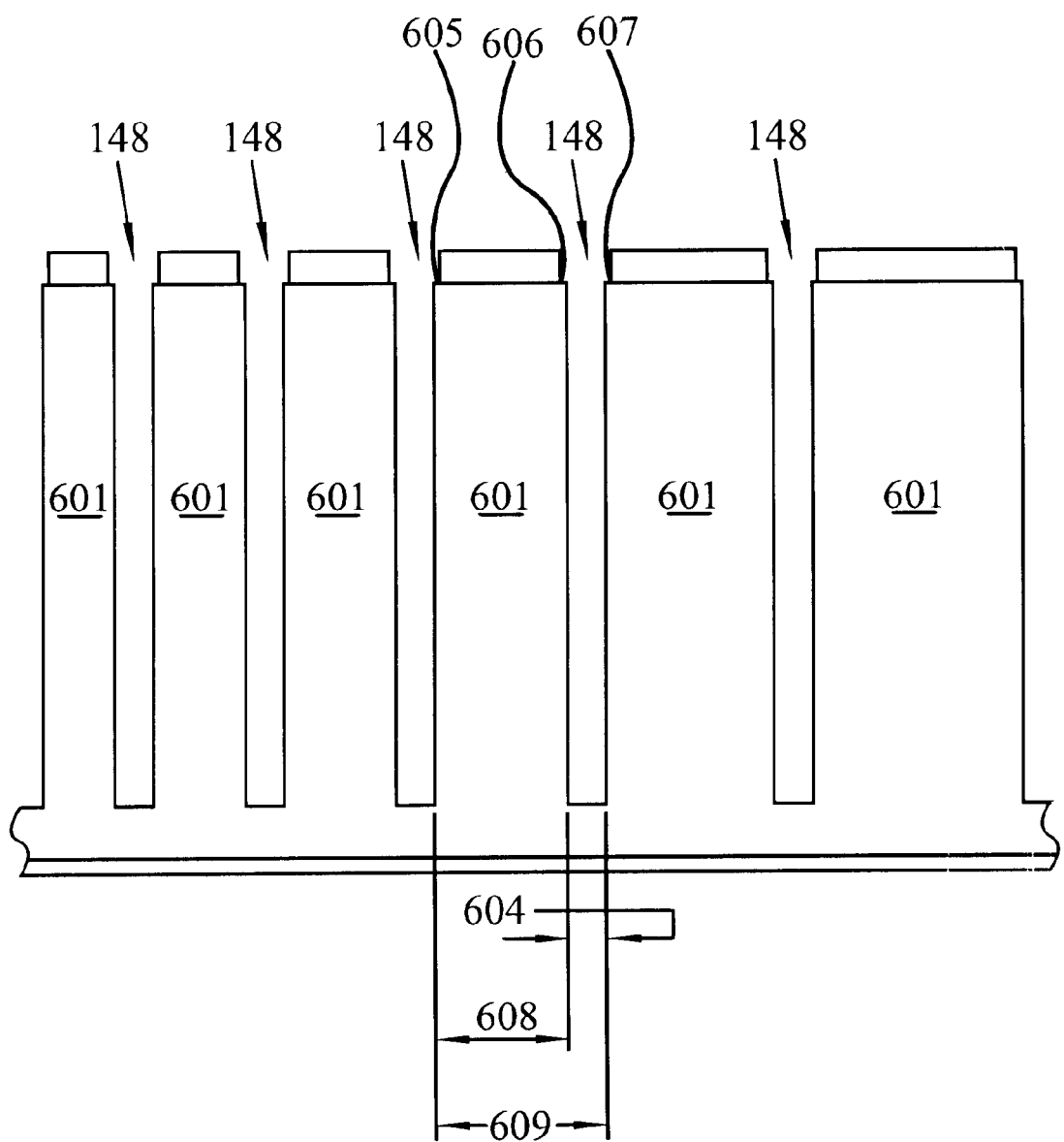
FIG. 6 is a close-up view of an exemplary composite cut shown in FIG. 5A.

An exemplary composite cut 148 in the substrate 130 can be seen in greater detail in FIG. 6. The width 604 of composite cut 148 is also known as the kerf 604, which is typically defined as the shortest distance from the leading edge 606 to the trailing edge 607 of a composite cut 148. The width 608 of post 601 is defined as the shortest distance from a trailing edge 605 of composite cut 148 to a leading edge 606 of the next composite cut 148. The shortest distance from a trailing edge 605 of a first composite cut 148 to the trailing edge 607 of the next composite cut 148 is defined as the pitch 609.

The word "middle" as used in this application with regards to the dimensions of the kerf, posts and pitch is defined to be the point or line on the surface of the substrate from which symmetrical changes may be based. The middle may, for example, be the point or line which provides the greatest transmission of ultrasonic signals. The middle is generally (although not necessarily) approximately equidistant from the edges of the piezoelectric substrate. That said, it is also understood that the pattern of composite cuts in the ceramic may or may not be symmetrical, and may or may not be based from a "middle" reference point or line.

The concentration of piezoelectric material in a given portion of a substrate is defined as the quantity of material in that portion of the cut substrate per unit volume of that portion of the uncut substrate. As described above, in one embodiment, reducing the width to height ratio in the middle of the aperture as compared to the edges results in frequency apodization. In another embodiment, increasing the concentration of piezoelectric material in the middle increases the signal strength transmitted through the center and results in amplitude apodization. This concentration or width to height change can be varied in several ways. For example, multiple constant width cuts can be made in piezoelectric substrate 130 with variable spacing 608 between these constant width cuts. This creates posts 601 (or fingers) of piezoelectric material that have variable widths 608.

Another exemplary method of varying the concentration of piezoelectric material is to maintain a constant width kerf 604 and to vary the post width 608 (the combination of which is equivalent to varying the pitch 609), as described above. Another method of varying the concentration piezoelectric material in a piezoelectric substrate 130 is to vary the width of the kerf 604 while maintaining a constant post width 608. In this method, pitch 609 also varies as appropriate. A third exemplary method is to vary both the kerf width 604 and the post 601 width 608. Variation in the width of the kerf 604 may be made by varying the types or the sizes of saws used to make composite cuts in piezoelectric substrate 130, or by using lasers or other cutting instruments known in the art which have the ability to create variable cut sizes. Other methods may also exist for varying the concentration of piezoelectric material.

In exemplary embodiments, with reference again to FIGS. 5A and 5B, an exemplary piezoelectric substrate 130 is shown with multiple composite cuts 148 made substantially perpendicular to the surface of the substrate layer. Posts 601 of piezoelectric material remain after composite cuts 148 have been made. In one exemplary embodiment, frequency and amplitude apodization may be achieved via composite cuts, as shown for example in FIG. 5A, where the width of post 601 is narrowest near middle 500 of the substrate and post width 608 becomes increasingly wider at greater distance from middle 500 in either direction 520 approaching either edge 510 of substrate 130. In another exemplary embodiment, amplitude apodization may be achieved via composite cuts, as shown for example in FIG. 5B, where the width of post 601 is shown to be widest near the middle 500 of the substrate and post width 608 becomes increasingly more narrow at greater distances from middle 500 in either direction 521 approaching either edge 510 of substrate 130. The size and location of composite cuts need not be limited to creating a pattern of increasing or decreasing post widths. Post width and kerf width may also be varied in any other pattern to achieve desired apodization.

Figure 7:
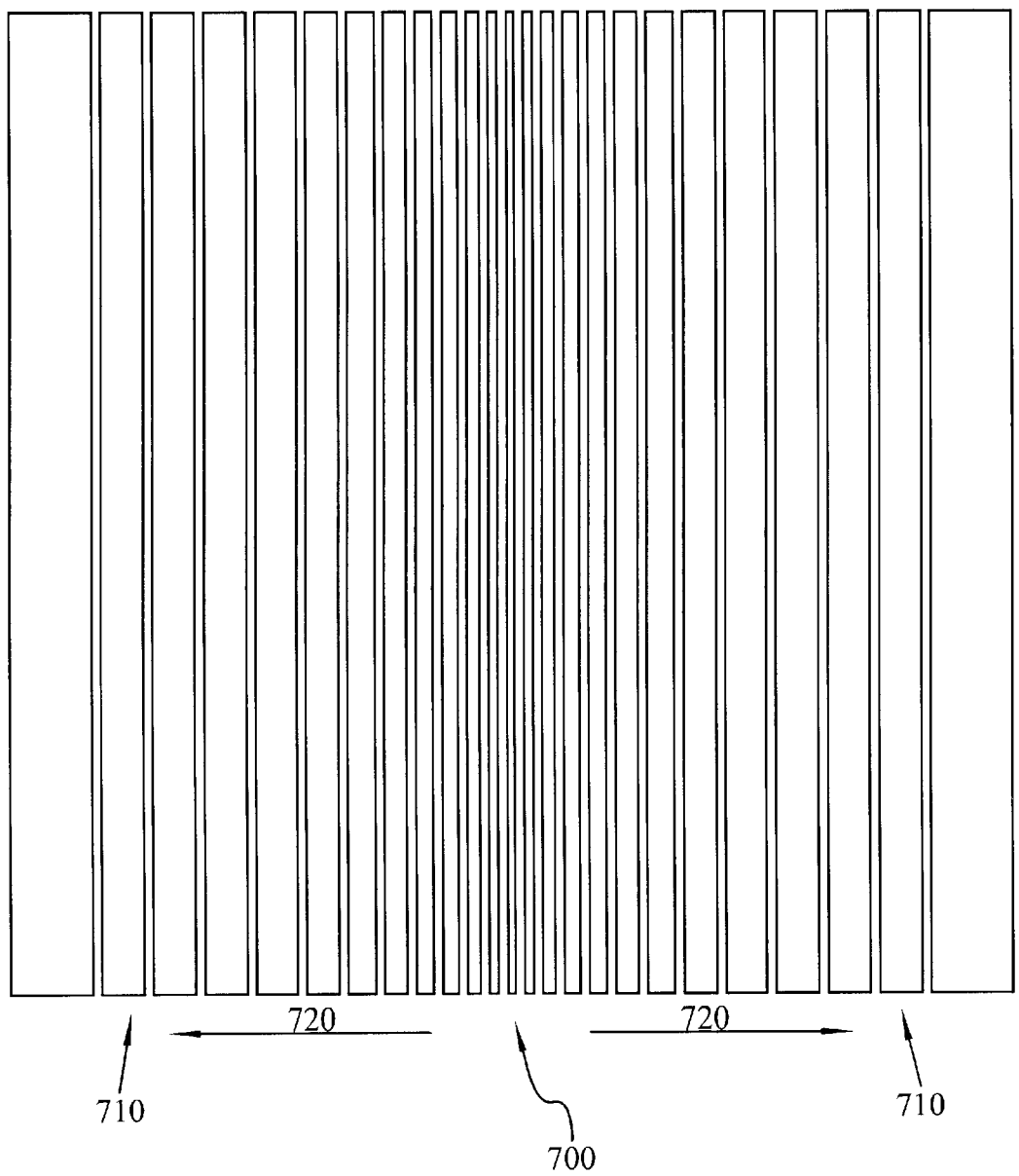
FIG. 7 is a top view showing an exemplary varying pitch profile.

FIG. 7 shows an exemplary view of the surface of a piezoelectric substrate with composite cuts made as described above with constant kerf composite cuts made such that post width 608 becomes increasingly wider away from middle 700 and towards edges 710 in the direction indicated by reference number 720, as shown in FIG. 7. In a further embodiment, and in addition to the composite cuts shown in FIG. 7, composite cuts can be made in piezoelectric substrate 130 at right angles to the composite cuts shown in FIG. 7, to create an array of piezoelectric elements similar to the array of elements shown in FIG. 2B but where the array is further apodized as explained herein. In another exemplary embodiment, composite cuts made such that post width 608 becomes increasingly narrow away from middle 700 and towards edges 710 in the direction indicated by reference number 720.

Typical kerf measurements, for an exemplary embodiment, may range from 25 to 30 microns. Corresponding pitch measurements, for example, may range from 50 to 100 microns. Corresponding post width measurements may range from 25 to 70 microns. although of course other embodiments with widely varying dimensions for kerf, pitch, and post width may also be used.

Many configurations of variable kerf width 604 and/or post width 608 are available which provide a variable concentration of piezoelectric material in the piezoelectric substrate and provide frequency and/or amplitude apodization. Customized kerf and post widths can be employed, for example. Also, various functions such as, for example, Bartlett, Blackman, Connes, Cosine, Uniform, Welch, and Hamming functions, or combinations thereof could be used in alternate embodiments. Furthermore, in one exemplary embodiment, concentration of piezoelectric material may vary according to either a Gaussian or Hanning distribution. For amplitude apodization, variation according to a Gaussian distribution can be achieved by varying the pitch according to the following equations:

$$\text{pitch} = p_i = \frac{y_i}{\sum y_i} AW;$$

and $$y_i = \frac{a}{\sigma\sqrt{2\pi}} e^{-1/2\left(\frac{x_i-\mu}{\sigma^2}\right)};$$

wherein: a=weighting constant; σ=standard deviation; μ=mean; and AW=Aperture width of crystal. In one exemplary embodiment, a=1; σ=4; μ=0; and AW=14 mm; however, other values may be used in connection with these formulas.

For amplitude apodization, variation according to a Hanning distribution can be achieved by varying the pitch according to the following equations:

$$\text{pitch} = p_i = \frac{y_i}{\sum y_i} AW;$$

and $$y_i = \alpha + (1-\alpha)\cos\left(\frac{2\pi x_i}{a}\right); \frac{-AW}{2} \leq x_i \leq \frac{AW}{2},$$

wherein: α=Hanning coefficient; a=weighting constant; and AW=Aperture width of crystal. In one exemplary embodiment, α=0.5, a=1, and AW=14 mm; however, other values may be used in connection with these formulas. For reference y is the composite cut pitch and x is related to the elevation aperture. For example, x may be chosen such that the smallest pitch is 40% smaller than the largest pitch. With regards to frequency apodization, variation according to a Gaussian or Hanning distribution is represented with equations modified as follows: For Gaussian, $$y_i = 1 - \frac{a}{\sigma\sqrt{2\pi}} e^{-1/2\left(\frac{x_i-\mu}{\sigma^2}\right)};$$

and for Hanning, $$y_i = 1 - \left(\alpha + (1-\alpha)\cos\left(\frac{2\pi x_i}{a}\right)\right).$$

Figure 8:
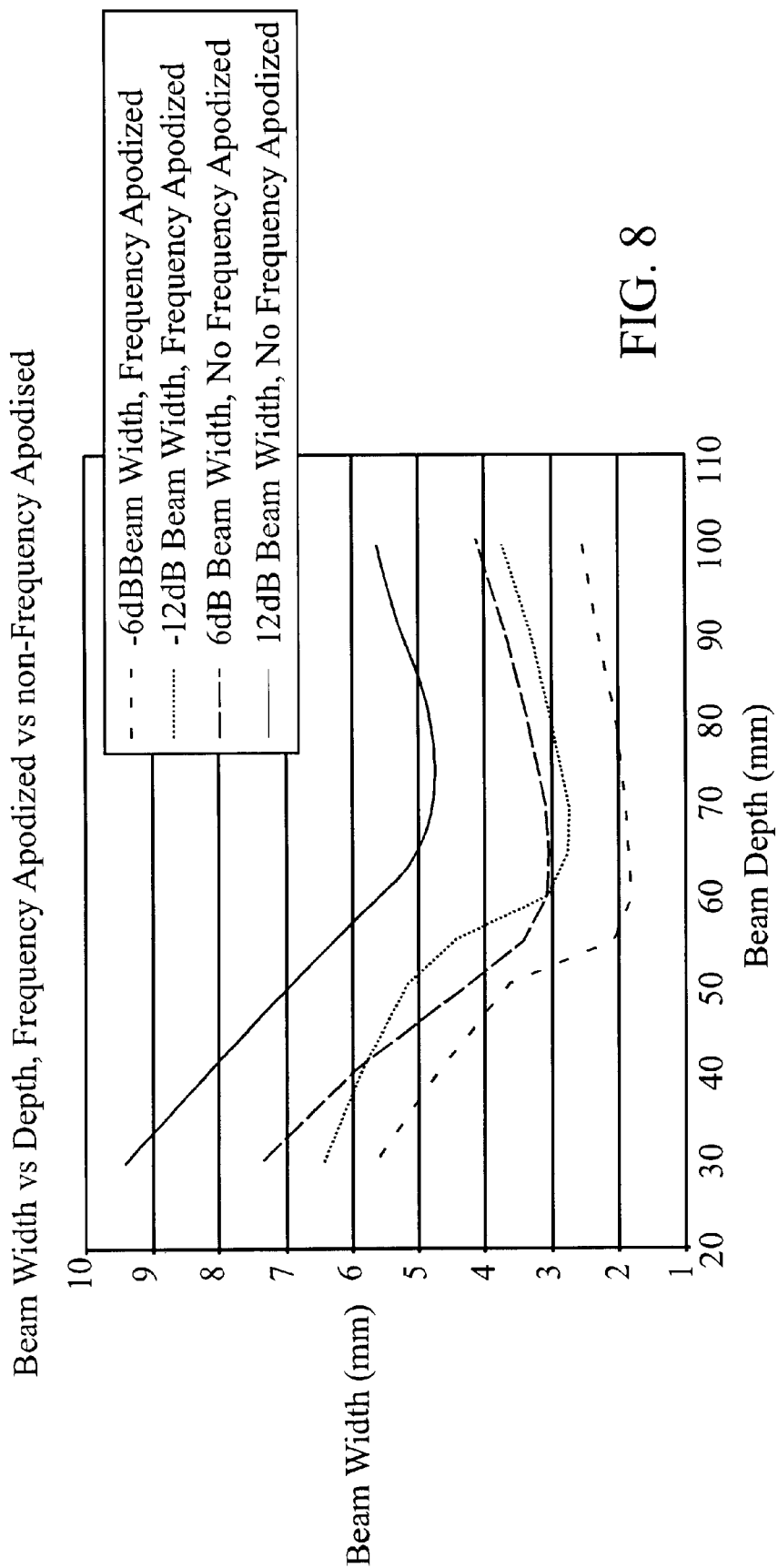
FIG. 8 is an exemplary graph of −6 dB and −12 dB beam width versus depth for a frequency apodization unit and a normal (non-frequency apodized) unit.

With reference to FIG. 8, an exemplary elevation beam profile graph (frequency apodized vs. non frequency apodized) is provided. In this figure the −6 dB and −12 dB elevation beam profiles have been mapped for a transducer with frequency apodization versus for a transducer without the apodization. As can be seen in FIG. 8, the resolution in both the near and the far-fields as well as in the focal zones has been vastly improved (about 50%) for the frequency apodized unit. It may also be observed that the focal zone or the near field-far field transition zone is essentially at the same location.

Figure 9:
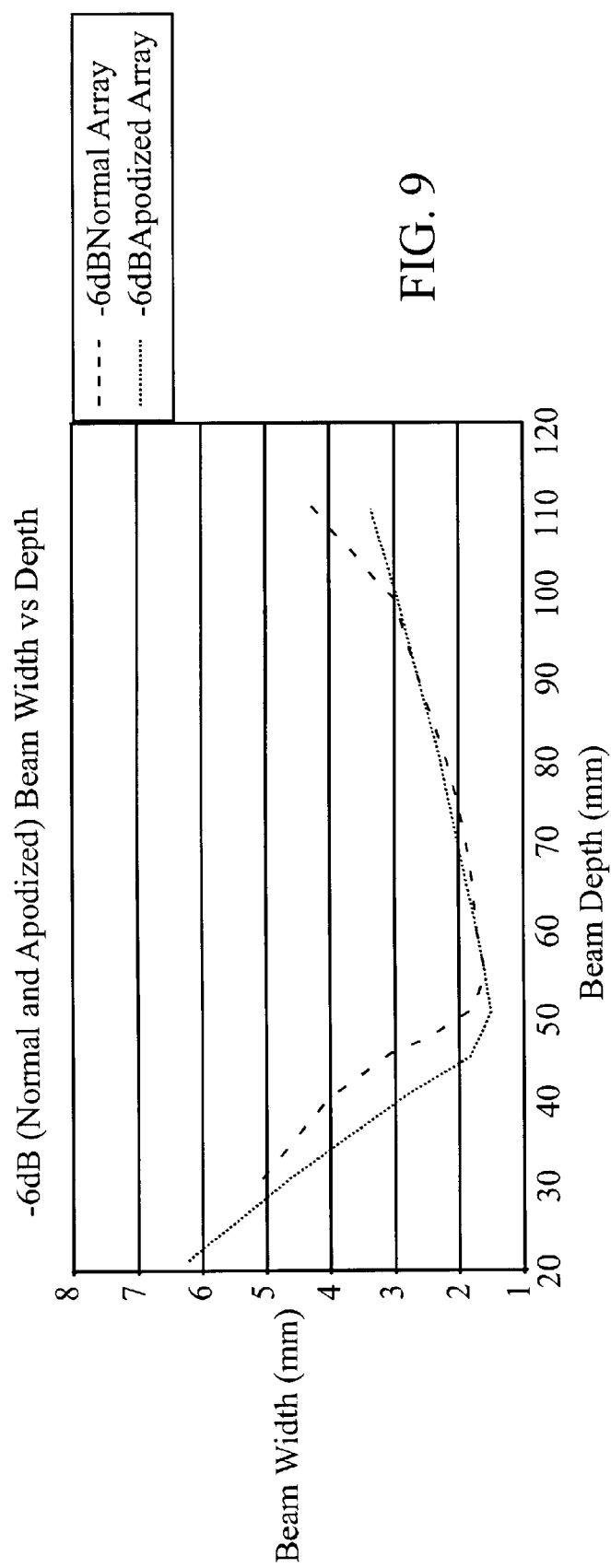
FIG. 9 is an exemplary graph of −6 dB beam width versus depth for an array (normal and amplitude apodized).
Figure 10:
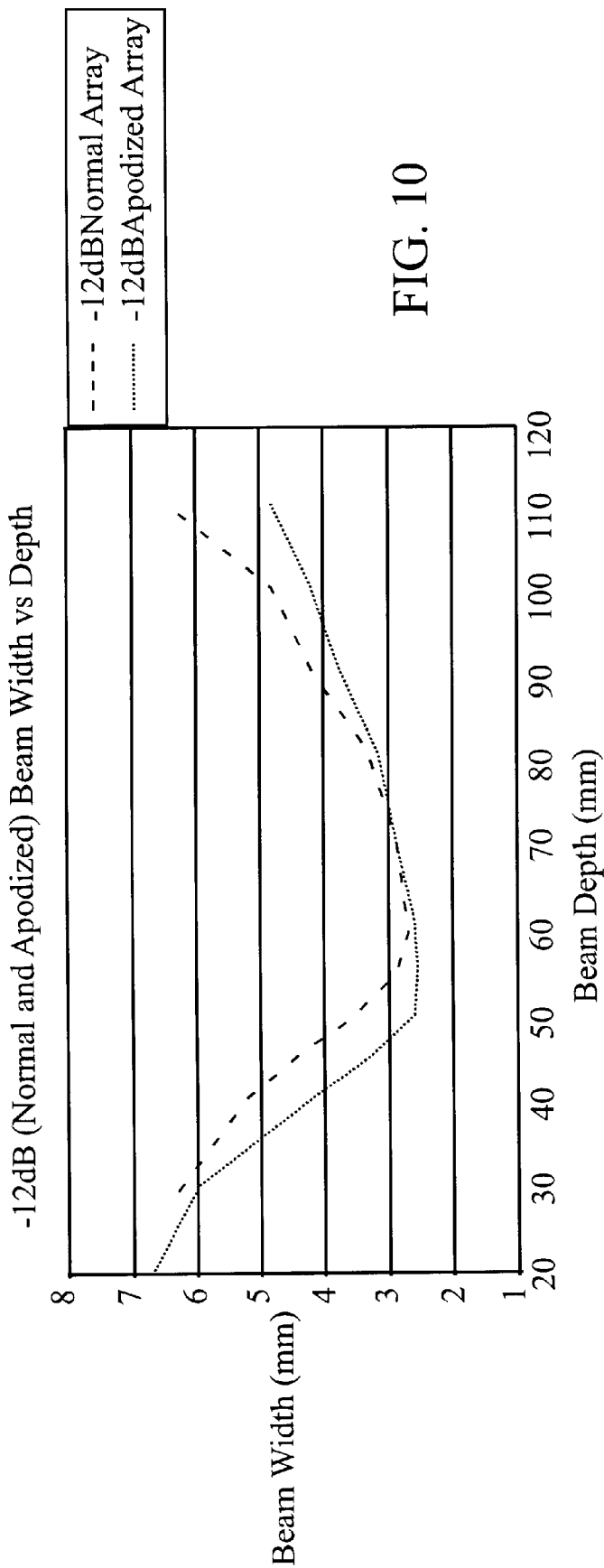
FIG. 10 is an exemplary graph of −12 dB beam width versus depth for an array (normal and amplitude apodized).

With reference to FIGS. 9 and 10, exemplary elevation beam profiles (amplitude apodized vs. non amplitude apodized) graphs are provided. In these Figures the −6 dB and −12 dB elevation beam profiles have been mapped for a transducer with amplitude apodization versus for a transducer without the apodization. As can be seen in FIGS. 9 and 10, the resolution in both the near and far fields is improved for the apodized transducer with the near field showing a more pronounced improvement. It may also be observed that the near field-far field transition has moved closer to the transducer for the apodized unit. This is probably because the effective mechanical elevation aperture is reduced due to the reduction in ceramic fill ratio going from the center to the edges of the aperture.

Other techniques may be combined in addition to the techniques described herein in the exemplary embodiment. For example, it is possible to perform full and partial poling of the piezoelectric elements which have been formed using the present invention. It is also possible to combine other techniques, such as applying signal-shaping functions to modify and improve the quality of the signals received from the transducer, utilizing acoustic blocking layers, polarization variations from one transducer element to another, and selective removal of metalization electrodes from select piezoelectric elements.

It will be appreciated that, upon completion of the composite cut, it is desirable to prepare acoustic matching layers. See FIG. 2A, 124 and 126. Acoustic matching layers may be formed of polymer or polymer composite materials as described in U.S. Pat. No. 5,637,800 (previously incorporated by reference). The same reference further describes an exemplary method of attaching the acoustic matching layers to the piezoelectric assembly, of forming the piezoelectric assembly into a desired shape, of preparing the formed piezoelectric and acoustic matching layer assembly to be configured in a housing, and providing appropriate electrical connections to the piezoelectric assembly.

Although the present invention has been described primarily in terms of ultrasonic transducers used in medical imaging applications, various aspects are useful in many other applications. For example, other medical transducers, non-destructive examinations of materials and devices, radio transmission, sonar, magnetic resonance imaging, optical applications, harmonic imaging, radio frequency arrays, optical defraction gradings, microwave, and other applications where high resolution collimated beams are required.

The corresponding structures, materials, acts, and equivalents of all elements in the claims below are intended to include any structure, material or act for performing the functions in combination with other claimed elements as specifically claimed. The scope of the invention should be determined by the appended claims and their legal equivalents, rather than by the examples given above. Additionally, the various steps included in any methods claims can be undertaken in any order or combined in any way while still falling under the ambit of the present invention.

What is claimed is:

1. A method of making an ultrasonic transducer comprising the steps of:

providing a piezoelectric material;

determining a plurality of kerf and pitch measurements, each of said plurality of kerf and pitch measurements corresponding to one of a plurality of composite cuts, wherein said plurality of kerf and pitch measurements and said plurality of composite cuts are determined such that a variable concentration of said piezoelectric material exists on said ultrasonic transducer, and wherein said plurality of composite cuts facilitates frequency apodization; and making said plurality of composite cuts within a single element in said piezoelectric material according to said plurality of kerf and said pitch measurements such that said piezoelectric material remaining between said composite cuts forms a plurality of posts; and wherein each post of said plurality of posts has a width defined by said kerf and pitch measurements and wherein said post widths are wider near the edges of said piezoelectric material and narrower near the middle of said transducer.

2. The method of claim 1 wherein:

said variable concentration of said piezoelectric material is achieved by varying said plurality of pitch measurements and keeping said plurality of kerf measurements substantially constant.

3. The method of claim 2 further including the steps of filling said plurality composite cuts with an epoxy.

4. The method of claim 2 wherein said epoxy is chosen to reduce clamping.

5. The method of claim 2 wherein:

said variation in said plurality of pitch measurements is determined such that said variable concentration of said piezoelectric material varies according to a Gaussian distribution.

6. The method of claim 1 wherein:

said variable concentration of said piezoelectric material is achieved by varying said plurality of kerf measurements and keeping said plurality of pitch measurements constant.

7. The method of claim 1 wherein:

said variable concentration of said piezoelectric material is achieved by varying said plurality of kerf measurements and varying said plurality of pitch measurements.

8. A method of making an ultrasonic transducer comprising the steps of:

providing a piezoelectric material; determining a plurality of kerf and pitch measurements, each of said plurality of kerf and pitch measurements corresponding to one of a plurality of composite cuts, wherein said plurality of kerf and pitch measurements and said plurality of composite cuts are determined such that a variable concentration of said piezoelectric material exists on said ultrasonic transducer; and making said plurality of composite cuts in said piezoelectric material according to said plurality of kerf and said pitch measurements such that said piezoelectric material remaining between said composite cuts forms a plurality of posts;

wherein said variable concentration of said piezoelectric material is achieved by varying said plurality of pitch measurements and keeping said plurality of kerf measurements substantially constant;

wherein said variation in said plurality of pitch measurements is determined such that said variable concentration of said piezoelectric material varies according to a Gaussian distribution; and wherein said variation in said Gaussian distribution is defined by the equation:

$$\text{pitch} = p_i = \frac{y_i}{\sum y_i} AW;$$

wherein, $$y_i = 1 - \frac{a}{\sigma\sqrt{2\pi}} e^{-1/2\left(\frac{x_i - \mu}{\sigma^2}\right)};$$

a=weighting constant; σ=standard deviation; $\mu$=mean; and AW=Aperture width of crystal.

9. A method of making an ultrasonic transducer comprising the steps of:

providing a piezoelectric material;

determining a plurality of kerf and pitch measurements, each of said plurality of kerf and pitch measurements corresponding to one of a plurality of composite cuts, wherein said plurality of kerf and pitch measurements and said plurality of composite cuts are determined such that a variable concentration of said piezoelectric material exists on said ultrasonic transducer; and making said plurality of composite cuts in said piezoelectric material according to said plurality of kerf and said pitch measurements such that said piezoelectric material remaining between said composite cuts forms a plurality of posts;

wherein said variable concentration of said piezoelectric material is achieved by varying said plurality of pitch measurements and keeping said plurality of kerf measurements substantially constant; and wherein said variation in said plurality of pitch measurements is determined such that said variable concentration of said piezoelectric material varies according to a Hanning distribution.

10. The method of claim 9, wherein:

said Hanning distribution is defined by the equation:

$$\text{pitch} = p_i = \frac{y_i}{\sum y_i} AW;$$

wherein, $$y_i = 1 - \left(\alpha + (1-\alpha)\cos\left(\frac{2\pi x_i}{a}\right)\right); \frac{-AW}{2} \leq x_i \leq \frac{AW}{2};$$

α=Hanning coefficient; a=weighting constant; and AW=Aperture width of crystal.

11. An ultrasonic transducer apparatus comprising:

a piezoelectric material;

a plurality of composite cuts in said piezoelectric material, wherein each of said composite cuts corresponds to one of a plurality of kerf measurements and one of a plurality of pitch measurements, and wherein said composite cuts form a variable concentration of said piezoelectric material on a single element of said ultrasonic transducer;

a plurality of posts formed of said piezoelectric material remaining between said composite cuts, wherein said plurality of posts have a variable post width defined by said kerf and pitch measurements; and a middle located on said piezoelectric material, wherein said composite cuts in said piezoelectric material are spaced such that post widths near said middle of said piezoelectric material are narrower than post widths formed by composite cuts further away from said middle, and wherein said variable post widths are configured to facilitate frequency apodization.

12. The apparatus of claim 11 wherein:

said plurality of pitch measurements varies; and said plurality of kerf measurements is constant.

13. The apparatus of claim 12 further including:

an epoxy integrated between each of said plurality of posts.

14. The apparatus of claim 13 wherein said epoxy is chosen to minimize clamping.

15. The apparatus of claim 11 wherein:

said plurality of kerf measurements varies; and said plurality of pitch measurements is constant.

16. The apparatus of claim 11 wherein:

said plurality of kerf measurements varies; and said plurality of pitch measurements varies.

17. An ultrasonic transducer apparatus comprising:

a piezoelectric material;

a plurality of composite cuts in said piezoelectric material, wherein each of said composite cuts corresponds to one of a plurality of kerf measurements and one of a plurality of pitch measurements, and wherein said composite cuts form a variable concentration of said piezoelectric material on said ultrasonic transducer; and a plurality of posts formed of said piezoelectric material remaining between said composite cuts;

wherein said plurality of pitch measurements varies; and said plurality of kerf measurements is constant;

wherein said variation in said plurality of pitch measurements is determined such that said variable concentration of said piezoelectric material varies according to a Gaussian distribution; and wherein said Gaussian distribution is defined by the equation:

$$\text{pitch} = p_i = \frac{y_i}{\sum y_i} AW;$$

wherein, $$y_i = 1 - \frac{a}{\sigma\sqrt{2\pi}} e^{-1/2\left(\frac{x_i - \mu}{\sigma^2}\right)};$$

a=weighting constant; σ=standard deviation; $\mu$=mean; and Aperture width of crystal.

18. An ultrasonic transducer apparatus comprising:

a piezoelectric material;

a plurality of composite cuts in said piezoelectric material, wherein each of said composite cuts corresponds to one of a plurality of kerf measurements and one of a plurality of pitch measurements, and wherein said composite cuts form a variable concentration of said piezoelectric material on said ultrasonic transducer; and a plurality of posts formed of said piezoelectric material remaining between said composite cuts;

wherein said plurality of pitch measurements varies; and said plurality of kerf measurements is constant;

wherein said variation in said plurality of pitch measurements is determined such that said variable concentration of said piezoelectric material varies according to a Hanning distribution; and wherein said Hanning distribution is defined by the equation:

$$\text{pitch} = p_i = \frac{y_i}{\sum y_i} AW;$$

wherein, $$y_i = 1 - \left(\alpha + (1-\alpha)\cos\left(\frac{2\pi x_i}{a}\right)\right); \quad \frac{-AW}{2} \leq x_i \leq \frac{AW}{2};$$

α=Hanning coefficient; a=weighting constant; and AW=Aperture width of crystal.

19. A transducer comprising:

a piezoelectric substrate, an acoustic matching layer, a series of composite cuts substantially perpendicular to an array axis substantially through the piezoelectric substrate forming a plurality of individual transducer posts in a single elements aligned along the array axis;

where-in said composite cuts are made according to at least one of the following:

a plurality of kerf measurements, and a plurality of pitch measurements; wherein said composite cuts give rise to a plurality of posts and a variable concentration of said piezoelectric material in said ultrasonic transducer; and wherein said kerf and pitch measurements facilitate frequency apodization.

* * * * *

UNITED STATES PATENT AND TRADEMARK OFFICE
CERTIFICATE OF CORRECTION

PATENT NO. : 6,726,631 B2  
DATED : April 27, 2004  
INVENTOR(S) : Hatangadi et al.

It is certified that error appears in the above-identified patent and that said Letters Patent is hereby corrected as shown below:

Column 16,
Line 12, between "and" and "Aperture" insert -- AW = --.

Signed and Sealed this

Sixth Day of September, 2005

JON W. DUDAS
*Director of the United States Patent and Trademark Office*